United States Patent [19]

Kobzina

[11] 4,030,906

[45] June 21, 1977

[54] HERBICIDAL N-HALOACETYL-1,2-DIHYDRO-4H-3,1-BENZOXAZINE

[75] Inventor: John W. Kobzina, Walnut Creek, Calif.

[73] Assignee: Chevron Research Company, San Francisco, Calif.

[22] Filed: Oct. 20, 1975

[21] Appl. No.: 623,842

Related U.S. Application Data

[62] Division of Ser. No. 509,979, Sept. 27, 1974, Pat. No. 3,917,592.

[52] U.S. Cl. .................................. 71/66; 71/67; 71/88
[51] Int. Cl.² .......................................... A01N 9/22
[58] Field of Search ............................. 71/66, 67, 88

[56] References Cited

UNITED STATES PATENTS

| | | | |
|---|---|---|---|
| 2,703,802 | 3/1955 | Norton | 71/88 X |
| 2,806,031 | 9/1957 | Rigterink | 71/88 X |
| 2,811,523 | 10/1957 | Rigterink | 71/88 X |
| 3,519,624 | 7/1970 | Huber-Emden | 424/248 X |

FOREIGN PATENTS OR APPLICATIONS 1,137,796  12/1968  United Kingdom

*Primary Examiner*—Joseph Paul Brust
*Attorney, Agent, or Firm*—J. A. Buchanan, Jr.; Dix A. Newell; Raymond Owyang

[57] ABSTRACT

Novel N-haloacetyl-1,2-dihydro-4H-3,1-benzoxazines which have utility as herbicides.

17 Claims, No Drawings

HERBICIDAL N-HALOACETYL-1,2-DIHYDRO-4H-3,1-BENZOXAZINE

This application is a division of U.S. Ser. No. 509,979, filed Sept. 27, 1974, now U.S. Pat. No. 3,917,592.

DESCRIPTION OF THE PRIOR ART

South African Pat. No. 6808449 [Chem. Abst. 72 79064s (1970)] discloses N-acetyl-3,4-dihydro-1H-2,3-benzoxazines which have anti-inflammatory activity.

British Patent 1,137,796 [Chem. Abstr. 70 106539t (1969)] discloses N-haloacylated 3,4-dihydro-2H-1,4-benzoxazines which are intermediates for the preparation of N-aminoacyl-3,4-dihydro-2H-1,4-benzoxazines.

U.S. Pat. No. 3,519,624 discloses N-haloacetyl-1,2-dihydro-1,3-benzoxazines which have antimicrobial, bactericidal and fungicidal properties.

DESCRIPTION OF THE INVENTION

The herbicidal N-haloacetyl-1,2-dihydro-4H-3,1-benzoxazine compounds of the invention are represented by the formula (I):

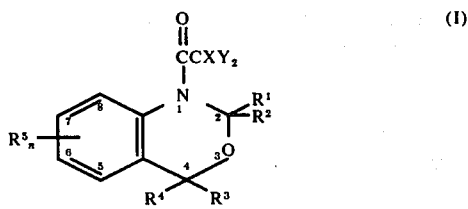

wherein X is fluoro, chloro or bromo; Y is hydrogen, fluoro, chloro or bromo; $R^1$, $R^2$, $R^3$ and $R^4$ individually are hydrogen or alkyl of 1 to 6 carbon atoms, preferably of 1 to 3 carbon atoms; $R^5$ is chloro, bromo or alkyl of 1 to 6 carbon atoms; and $n$ is 0, 1 or 2.

Preferably $R^5$ is alkyl of 1 to 6 carbons, more preferably of 1 to 3 carbon atoms. Most preferably $R^5$ is at the 8th position of the benzoxazine ring. Preferably $n$ is 0 or 1. Preferably Y is hydrogen.

In part because of their utility for the control of aquatic weeds, a preferred class of compounds of formula (I) is that wherein X is bromo. In this preferred class, Y is preferably hydrogen or bromo, more preferably hydrogen.

Representative compounds of formula (I) include:
1-dibromoacetyl-1,2-dihydro-4H-3,1-benzoxazine
1-trichloroacetyl-1,2-dihydro-4H-3,1-benzoxazine
1-chloroacetyl-7,8-dimethyl-1,2-dihydro-4H-3,1-benzoxazine
1-fluoroacetyl-5,6-dichloro-1,2-dihydro-4H-3,1-benzoxazine
1-chloroacetyl-2,4-dipropyl-1,2-dihydro-4H-3,1-benzoxazine
1-chloroacetyl-5-chloro-8-methyl-1,2-dihydro-4H-3,1-benzoxazine and
1-dichloroacetyl-7-methyl-1,2-dihydro-4H-3,1-benzoxazine.

The compounds of the invention are prepared as depicted in reactions 1 and 2:

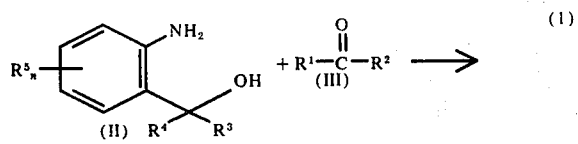

wherein X, Y, $R^1$, $R^2$, $R^3$, $R^4$, $R^5$ and $n$ have the same significance as previously defined, and B is an acid acceptor.

The condensation reaction (1) is conducted by reacting the aminobenzyl alcohol (II) with the aldehyde or ketone (III) at a temperature of 0° to 100° C. in an inert diluent. Generally, at least one mol of aldehyde or ketone (III) is used per mol of alcohol (II). The benzoxazine product (IV) is isolated by conventional procedures such as extraction, distillation or chromatography.

The alkylation reaction (2) is conducted by contacting the benzoxazine (IV), the haloacetyl halide (V) and the acid acceptor in an inert diluent at a temperature of about 0° to 100° C. The reactants (IV) and (V) and the acid acceptor are generally used in substantially equimolar amounts, although an excess of the acid acceptor may be used. Suitable acid acceptors include trialkylamines and pyridine compounds. The product (I) is isolated and purified by conventional procedures such as extraction, distillation, chromatography, crystallization, etc.

EXAMPLES

EXAMPLE 1 — Preparation of 1-chloroacetyl-4,4-dimethyl-1,2-dihydro-4H-3,1-benzoxazine A 30.2-g (0.2 mol) sample of methyl 2-aminobenzoate in 150 ml diethyl ether was added dropwise to a solution of methyl magnesium iodide (prepared from 19.4 g of Mg and 127.8 g of methyl iodide) in 150 ml diethyl ether. The reaction mixture was then heated under reflux for 1 hour, cooled, and diluted with 200 ml of saturated aqueous ammonium chloride solution. The resulting aqueous mixture was extracted with ether. The ether extracts were dried over magnesium sulfate and evaporated to give 19.1 g of α,α-dimethyl-2-aminobenzyl alcohol.

An 8.25-ml solution of 37% aqueous formaldehyde (0.099 mol) was added over 5 minutes to a cooled (0° C.) mixture of 10 g (0.066 mol) α,α-dimethyl-2-aminobenzyl alcohol in 50 ml water. The reaction mixture was then diluted with 50 ml benzene and vigorously stirred for 5 minutes. The aqueous layer was separated and extracted with benzene. The benzene layer of the reaction mixture and the benzene extracts were combined, dried over magnesium sulfate and evaporated. The resulting oil was distilled through a short column to give 6.3 g (b.p. 120°–125° C. at 0.1 mm of Hg) of 4,4-dimethyl-1,2-dihydro-4H-3,1-benzoxazine, as a colorless oil. Elemental analysis showed: %C, calc. 73.6, found 68.3: %H, calc. 8.0, found 7.6; %N, calc. 8.6, found 8.6.

A solution of 1.73 g (0.015 mol) α-chloroacetyl chloride in 5 ml methylene chloride was added dropwise to a solution of 2.5 g (0.015 mol) 4,4-dimethyl-1,2-dihydro-4H-3,1-benzoxazine and 1.55 g (0.015 mol) triethylamine in 75 ml methylene chloride. The reaction mixture was stirred at about 25° C. for 2 hours, washed with water, dried over magnesium sulfate and evaporated to give a crystalline solid. The solid was washed with ether/hexane and dried to give 2.75 g of 1-chloroacetyl-4,4-dimethyl-1,2-dihydro-4H-3,1-benzoxazine, m.p. 80°–84° C, as a brown solid.

EXAMPLE 2 — Preparation of 1-chloroacetyl-2,2,4,4-tetramethyl-1,2-dihydro-4H-3,1-benzoxazine

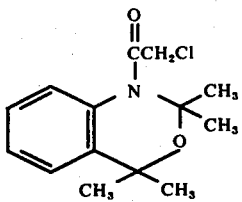

A solution of 15 g (0.1 mol) α,α-dimethyl-2-aminobenzyl alcohol and 5.7 g (0.1 mol) acetone in 120 ml of benzene was heated under reflux in a Dean-Stark trap for 3 hours. About 1.5 ml of water was separated from the reaction mixture. The benzene solution was then evaporated to give an oil which solidified on standing. Recrystallization from ethanol-water gave 5.2 g 2,2,4,4-tetramethyl-1,2-dihydro-4H-3,1-benzoxazine, as a white solid.

A solution of 2.95 g (0.026 mol) α-chloroacetyl chloride in 5 ml methylene chloride was added dropwise to a solution of 5 g (0.026 mol) 2,2,4,4-tetramethyl-1,2-dihydro-4H-3,1-benzoxazine and 2.64 g (0.026 mol) triethylamine in 70 ml methylene chloride. The reaction mixture was stirred at about 25° C. for 1.5 hours, washed with water, dried over magnesium sulfate and evaporated. The residue was chromatographed on silica gel (20% ether-80% hexane eluant) to give 3.0 g of 1-chloroacetyl-2,2,4,4-tetramethyl-1,2-dihydro-4H-3,1-benzoxazine, m.p. 52°–57° C., as a white solid.

Other compounds of the present invention were prepared by procedures similar to the above examples. These compounds and the compounds of Examples 1 and 2 are tabulated in Table I.

UTILITY

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. Some may be selective with respect to the type of application and/or type of weed.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atapulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally for both pre- and post-emergent control, the herbicidal compounds of the invention are applied at rates of 0.2 to 60 kg/ha, and the preferred rate is in the range 0.5 to 40 kg/ha.

Pre- and post-emergent herbicidal tests on representative compounds of the invention were made using the following methods:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 mcg/cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

Post-Emergent Test

The test compound was formulated in the same manner as described above for the pre-emergent test. The concentration of the test compound in this formulation was 5,000 ppm. This formulation was uniformly sprayed on 2 similar pots of 24-day-old plants (approximately 15 to 25 plants per pot) at a dose of 33 mcg/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill.

The compounds of the invention wherein X is bromo, i.e., the N-bromoacetyl-1,2-dihydro-4H-3,1-benzoxazines, are useful for controlling aquatic weeds such as Euglena, Spirogyra, Nitella, Lemna, Elodea, Hornwort and Azolla. They may be used to control such aquatic weeds in aqueous bodies such as lakes, streams, canals, pools, aqueous industrial effluents, cooling towers, and the like. When so used, a biocidal quantity of one or more of the N-bromoacetyl-benzoxazines of the invention is added to the aqueous growth environment of the weeds. Usually, this dosage will range between about 0.1 and 10 ppm. These compounds may be applied to the aqueous growth environments of such weeds as dispersible powders or in solution with water-miscible solvents.

Representative N-bromoacetylbenzoxazines of this invention were tested as algicides by the following method. An acetone solution of the test compound and a surfactant was prepared. This solution was mixed with a nutrient broth in a quantity sufficient to give a concentration of 2 ppm test compound. Three 150-ml specimen cups were filled with this mixture. Samples of the test algae were added to each specimen cup and the cups where then placed in an environment chamber for incubation. The cups were observed periodically for alga growth. The algicidal effectiveness of the test compound was determined based on a final observation of alga growth after 8 days. The results of these tests, reported as the average of the 3 specimen cups on a 0-to-100 basis — 0 indicating no effectiveness and 100 indicating complete effectiveness — are reported in Table III.

TABLE I

| No. | Compound | Melting point, °C. | Halogen Analysis Calc. | Halogen Analysis Found |
|---|---|---|---|---|
| 1 | 1-chloroacetyl,4,4-dimethyl-1,2-dihydro-4H-3,1-benzoxazine | 80–84 | 14.8 | 15.8 |
| 2 | 1-bromoacetyl-4,4-dimethyl-1,2-dihydro-4H-3,1-benzoxazine | 78–80.5 | 4.9* | 5.1* |
| 3 | 1-chloroacetyl-2,2,4,4-tetramethyl-1,2-dihydro-4H-3,1-benzoxazine | 52–57 | 13.2 | 11.8 |
| 4 | 1-bromoacetyl-1,2-dihydro-4H-3,1-benzoxazine | Oil | 31.2 | 30.5 |
| 5 | 1-chloroacetyl-1,2-dihydro-4H-3,1-benzoxazine | Oil | 16.8 | 18.5 |
| 6 | 1-chloroacetyl-2,2-dimethyl-1,2-dihydro-4H-3,1-benzoxazine | 47–49 | 14.8 | 15.4 |
| 7 | 1-chloroacetyl-2,4,4-trimethyl-1,2-dihydro-4H-3,1-benzoxazine | Oil | 14.0 | 14.3 |
| 8 | 1-chloroacetyl-2-ethyl-2,4,4-trimethyl-1,2-dihydro-4H-3,1-benzoxazine | Oil | 12.6 | 12.0 |
| 9 | 1-bromoacetyl-2,4,4-trimethyl-1,2-dihydro-4H-3,1-benzoxazine | 54–56 | 26.8 | 26.6 |
| 10 | 1-chloroacetyl-2-methyl-1,2-dihydro-4H-3,1-benzoxazine | Oil | 15.7 | 15.1 |
| 11 | 1-chloroacetyl-8-methyl-1,2-dihydro-4H-3,1-benzoxazine | 87–91 | 15.7 | 16.1 |
| 12 | 1-chloroacetyl-2,4,4-8-tetramethyl-1,2-dihydro-4H-3,1-benzoxazine | 64–66 | 13.2 | 13.0 |
| 13 | 1-bromoacetyl-2,4,4,8-tetramethyl-1,2-dihydro-4H-3,1-benzoxazine | 70–72 | 25.6 | 24.2 |
| 14 | 1-chloroacetyl-2-methyl-4,4,-diethyl-1,2-dihydro-4H-3,1-benzoxazine | Oil | 12.6 | 12.3 |
| 15 | 1-bromoacetyl-2-methyl-4,4-diethyl-1,2-dihydro-4H-3,1-benzoxazine | Oil | 24.5 | 22.7 |
| 16 | 1-chloroacetyl-2,4-dimethyl-4-ethyl-1,2-dihydro-4H-3,1-benzoxazine | Oil | 13.2 | 12.2 |
| 17 | 1-chloroacetyl-2,4-dimethyl-4-ethyl-1,2-dihydro-4H-3,1-benzoxazine | 39–41 | 14.8 | 14.9 |
| 18 | 1-bromoacetyl-2,4-dimethyl-4-ethyl-1,2-dihydro-4H-3,1-benzoxazine | Oil | 28.1 | 28.1 |
| 19 | 1-chloroacetyl-2,2,4-trimethyl-4-ethyl-1,2-dihydro-4H-3,1-benzoxazine | Oil | 12.6 | 11.3 |
| 20 | 1-chloroacetyl-2-methyl-8-chloro-1,2-dihydro-4H-3,1-benzoxazine | Oil | 27.2 | 25.0 |
| 21 | 1-chloroacetyl-2,2,4-trimethyl-1,2-dihydro-4H-3,1-benzoxazine | 83–84 | 14.0 | 13.6 |
| 22 | 1-bromoacetyl-2,2,4-trimethyl-1,2-dihydro-4H-3,1-benzoxazine | 83–90 | 26.8 | 25.0 |
| 23 | 1-chloroacetyl-2,8-dimethyl-1,2-dihydro-4H-3,1-benzoxazine | 72–75 | 14.8 | 14.0 |
| 24 | 1-chloroacetyl-2-methyl-8-ethyl-1,2-dihydro-4H-3,1-benzoxazine | Oil | 14.0 | 12.8 |
| 25 | 1-chloroacetyl-2,4,4-trimethyl-1,2-dihydro-4H-3,1-benzoxazine | 88–90 | 12.6 | 12.7 |
| 26 | 1-chloroacetyl-2,2,4,6-tetramethyl-1,2-dihydro-4H-3,1-benzoxazine | Oil | 13.2 | 12.3 |
| 27 | 1-chloroacetyl-2,6-dimethyl-1,2-dihydro-4H-3,1-benzoxazine | Oil | 14.8 | 14.8 |
| 28 | 1-chloroacetyl-4,4-dimethyl-8-ethyl-1,2-dihydro-4H-3,1-benzoxazine | 76–78 | 13.3 | 14.0 |

*Nitrogen analysis

TABLE II

| | Herbicidal Effectiveness | | | | | |
|---|---|---|---|---|---|---|
| No. | O | W | C | M | P | L |
| 2 | 0 | 0 | 0 | 75* | 85* | 85* |
| 3 | 20 | 100 | 50 | — | — | — |
| 4 | 0 | 0 | 0 | 10* | 30* | 35* |
| 5 | 0 | 55 | 40 | 25 | 75 | 20 |
| 6 | 10 | 75 | 10 | 0 | 0 | 0 |
| 7 | 40 | 100 | 95 | 0 | 95 | 70 |
| 8 | 30 | 60 | 0 | 0 | 0 | 0 |
| 9 | 10 | 75 | 60 | 0 | 10 | 0 |
| 10 | 0 | 100 | 60 | 30 | 65 | 25 |
| 11 | 83 | 100 | 100 | 0 | 15 | 25 |
| 12 | 100 | 100 | 100 | 95 | 100 | 98 |
| 13 | 60 | 98 | 98 | 25 | 95 | 45 |
| 14 | 15 | 93 | 93 | 0 | 95 | 95 |
| 15 | 35 | 20 | 30 | 0 | 25 | 35 |
| 16 | 0 | 100 | 95 | 0 | 0 | 90 |
| 17 | 0 | 98 | 15 | 0 | 30 | 60 |
| 18 | 0 | 20* | 0 | 35* | 40* | 50* |
| 19 | 10 | 98 | 0 | 0 | 0 | 0 |
| 20 | 10 | 85 | 0 | 0 | 0 | 0 |
| 21 | 10 | 100 | 15 | 10 | 0 | 0 |
| 22 | 0 | 0 | 0 | 10* | 15* | 15* |
| 23 | 0 | 90 | 70 | 0 | 0 | 0 |
| 24 | 20 | 85 | 30 | 0 | 0 | 0 |
| 25 | 55 | 100 | 100 | 80 | 100 | 90 |
| 26 | 10 | 80 | 0 | 0 | 0 | 0 |
| 27 | 0 | 95 | 0 | 0 | 0 | 0 |
| 28 | 93 | 100 | 100 | 85 | 100 | 93 |

*Post-emergent test
O = Wild Oats (*Avenua fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

TABLE III

| | Algicidal Effectiveness, % Control | | | |
| --- | --- | --- | --- | --- |
| Compound No. | Elodea | Lemna | Hornwort | Azolla |
| 4 | 90 | 99 | 100 | 82 |
| 2 | 60 | — | — | — |
| 13 | 60 | — | — | — |

What is claimed is:

1. A method for controlling undesirable vegetation which comprises applying to the vegetation or the locus thereof a herbicidally effective amount of the compound of the formula

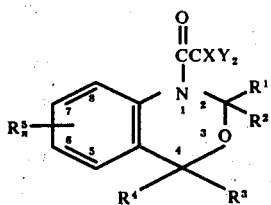

wherein X is fluoro, chloro or bromo, Y is hydrogen, fluoro, chloro, or bromo, $R^1$ is hydrogen or alkyl of 1 to 6 carbon atoms, $R^2$ is hydrogen or alkyl of 1 to 6 carbon atoms, $R^3$ is hydrogen or alkyl of 1 to 6 carbon atoms, $R^4$ is hydrogen or alkyl of 1 to 6 carbon atoms, $R^5$ is chloro, bromo or alkyl of 1 to 6 carbon atoms, and $n$ is 0, 1 or 2.

2. The method of claim 1 wherein Y is hydrogen, $R^1$ is alkyl of 1 to 6 carbon atoms, $R^3$ is alkyl of 1 to 6 carbon atoms; and $R^4$ is alkyl of 1 to 6 carbon atoms.

3. The method of claim 2 wherein $R^5$ is alkyl of 1 to 6 carbon atoms and n is 1.

4. The method of claim 3 wherein X is chloro, $R^1$ is alkyl of 1 to 3 carbon atoms, $R^2$ is hydrogen, $R^3$ is alkyl of 1 to 3 Carbon atoms, $R^4$ is alkyl of 1 to 3 carbon atoms and $R^5$ is alkyl of 1 to 3 carbon atoms and is substituted at the eighth position of the benzoxazine ring.

5. The method of claim 2 wherein $R^5$ is chloro or bromo and $n$ is 1.

6. The method of claim 1 wherein the compound is 1-Chloroacetyl-4,4-dimethyl-8-ethyl-1,2-dihydro-4H-3,1-benzoxazine.

7. A method for controlling aquatic weeds which comprises applying to the aqueous growth environment of said weeds a biocidally effective amount of the compound of the formula defined in claim 1 wherein Y is hydrogen and X is bromo.

8. The method of claim 7 wherein the compound is 1-bromoacetyl-1,2-dihydro-4H-3,1-benzoxazine.

9. A method for controlling algae which comprises applying to the agrowth environment of said algae an algicidally effective amount of the compound of the formula defined in claim 1 wherein Y is hydrogen and X is bromo.

10. The method of claim 9 wherein the compound is 1-bromoacetyl-1,2-dihydro-4H-3,1-benzoxazine.

11. An herbicidal composition comprising from about 0.01% to 95% by weight, based on the entire composition, of the compound of the formula

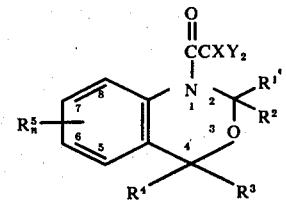

wherein X is fluoro, chloro or bromo, Y is hydrogen, $R^1$ is alkyl of 1 to 6 carbon atoms, $R^2$ is hydrogen or alkyl of 1 to 6 carbon atoms, $R^3$ is alkyl of 1 to 6 carbon atoms, $R^4$ is hydrogen or alkyl of 1 to 6 carbon atoms, $R^5$ is chloro, bromo or alkyl of 1 to 6 carbon atoms and $n$ is 0, 1 or 2, and an inert carrier.

12. The composition of claim 11 wherein Y is hydrogen, $R^1$ is alkyl of 1 to 6 carbon atoms, $R^3$ is alkyl of 1 to 6 carbon atoms, and $R^4$ is alkyl of 1 to 6 carbon atoms.

13. The composition of claim 12 wherein X is chloro, $R^1$ is alkyl of 1 to 3 carbon atoms, $R^2$ is hydrogen, $R^3$ is alkyl of 1 to 3 carbon atoms, $R^4$ is alkyl of 1 to 3 carbon atoms, $R^5$ is alkyl of 1 to 3 carbon atoms and is substituted at the 8th position of the benzoxazine ring and $n$ is 1.

14. The composition of claim 12 wherein $R^5$ is chloro or bromo and $n$ is 1.

15. The composition of claim 11 wherein the compound is 1-chloroacetyl-4,4-dimethyl-8-ethyl-1,2-dihydro-4H-3,1-benzoxazine.

16. The method of claim 1 wherein X is chloro, Y is hydrogen, $R^1$ is hydrogen, $R^2$ is hydrogen, $R_3$ is alkyl of 1 to 3 carbon atoms, $R^4$ is alkyl of 1 to 3 carbon atoms, $R^5$ is alkyl of 1 to 3 carbon atoms and is substituted at the 8th position of the benzoxazine ring, and $n$ is 1.

17. The composition of claim 11 wherein X is chloro, Y is hydrogen, $R^1$ is hydrogen, $R^2$ is hydrogen, $R^3$ is alkyl of 1 to 3 carbon atoms, $R^4$ is alkyl of 1 to 3 carbon atoms, $R^5$ is alkyl of 1 to 3 carbon atoms and is substituted at the 8th position of the benzoxazine ring and $n$ is 1.

* * * * *